(12) United States Patent
Yamada

(10) Patent No.: US 11,344,265 B2
(45) Date of Patent: May 31, 2022

(54) RADIOGRAPHY SYSTEM AND RADIOGRAPHY METHOD

(71) Applicant: CANON KABUSHIKI KAISHA, Tokyo (JP)

(72) Inventor: Daisuke Yamada, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 99 days.

(21) Appl. No.: 16/458,685

(22) Filed: Jul. 1, 2019

(65) Prior Publication Data

US 2019/0320990 A1 Oct. 24, 2019

Related U.S. Application Data

(63) Continuation of application No. PCT/JP2017/047159, filed on Dec. 28, 2017.

(30) Foreign Application Priority Data

Jan. 18, 2017 (JP) .............................. JP2017-006979

(51) Int. Cl.
*A61B 6/00* (2006.01)
(52) U.S. Cl.
CPC .......... *A61B 6/4208* (2013.01); *A61B 6/4266* (2013.01); *A61B 6/4476* (2013.01); *A61B 6/5241* (2013.01); *A61B 6/54* (2013.01)

(58) Field of Classification Search
CPC ... A61B 6/4208; A61B 6/4266; A61B 6/4476; A61B 6/5241; A61B 6/54; A61B 6/547
See application file for complete search history.

(56) References Cited

U.S. PATENT DOCUMENTS

2016/0074001 A1\* 3/2016 Matsushita .......... A61B 6/4233
378/62
2016/0220213 A1 8/2016 Miyamoto

FOREIGN PATENT DOCUMENTS

| JP | 2012-000332 A | 1/2012 |
| JP | 2012-040140 A | 3/2012 |
| JP | 2016-059534 A | 4/2016 |
| JP | 2016-140515 A | 8/2016 |

\* cited by examiner

*Primary Examiner* — Dani Fox
(74) *Attorney, Agent, or Firm* — Canon U.S.A., Inc. IP Division

(57) ABSTRACT

To appropriately perform long-sized imaging even in the case of performing long-sized imaging using different types of radiation detectors, a radiography system for generating a long-sized image by combining a plurality of items of image data obtained from a plurality of radiation detectors 120, 122, and 124 includes a determination unit 202, which determines whether or not long-sized imaging is possible on the basis of identification information and position information of the plurality of radiation detectors 120, 122, and 124.

19 Claims, 9 Drawing Sheets

RADIOGRAPHY SYSTEM AND RADIOGRAPHY METHOD

CROSS-REFERENCE TO RELATED APPLICATIONS

This application is a Continuation of International Patent Application No. PCT/JP2017/047159, filed Dec. 28, 2017, which claims the benefit of Japanese Patent Application No. 2017-006979, filed Jan. 18, 2017, both of which are hereby incorporated by reference herein in their entirety.

TECHNICAL FIELD

The present invention relates to a radiography system and a radiography method for performing imaging using radiation.

BACKGROUND ART

In recent years in, for example, the medical field, imaging with a wide observation area (hereinafter referred to as long-sized imaging) is performed, as in the case of capturing an image of the entire spinal cord or lower limbs or the entire body of a subject. PTL 1 discloses a radiography system capable of performing long-sized imaging by performing imaging while arranging a plurality of radiation detectors (radiography apparatuses).

CITATION LIST

Patent Literature

PTL 1 Japanese Patent Laid-Open No. 2012-040140

In PTL 1, in the case of performing imaging while arranging a plurality of radiation detectors so that some of the radiation detectors overlap, a radiation detector structure arranged at a position closer to a radiation generator appears in image data obtained by a radiation detector arranged at a position farther from the radiation generator.

In addition, long-sized imaging may be performed using different types of radiation detectors. In the case where a radiation detector arranged at a position closer to a radiation generator includes many complicated structures, the complicated structures appear in image data output from a radiation detector arranged at a position farther from the radiation generator. As a result, the image quality of a long-sized image generated by long-sized imaging is degraded.

Therefore, it is an object of the present invention to provide a radiography system and a radiography method capable of appropriately performing long-sized imaging even in the case of performing long-sized imaging using different types of radiation detectors.

SUMMARY OF INVENTION

To achieve the object of the present invention, a radiography system for generating a long-sized image by combining a plurality of items of image data obtained from a plurality of radiation detectors includes a determination unit that determines whether or not long-sized imaging is possible on the basis of identification information and position information of the plurality of radiation detectors.

According to the present invention, long-sized imaging can be appropriately performed even in the case of performing long-sized imaging using different types of radiation detectors.

Further features of the present invention will become apparent from the following description of exemplary embodiments with reference to the attached drawings.

DESCRIPTION OF EMBODIMENTS

Hereinafter, preferred embodiments of the present invention will be described with reference to the accompanying drawings.

First Embodiment

Figure 1:
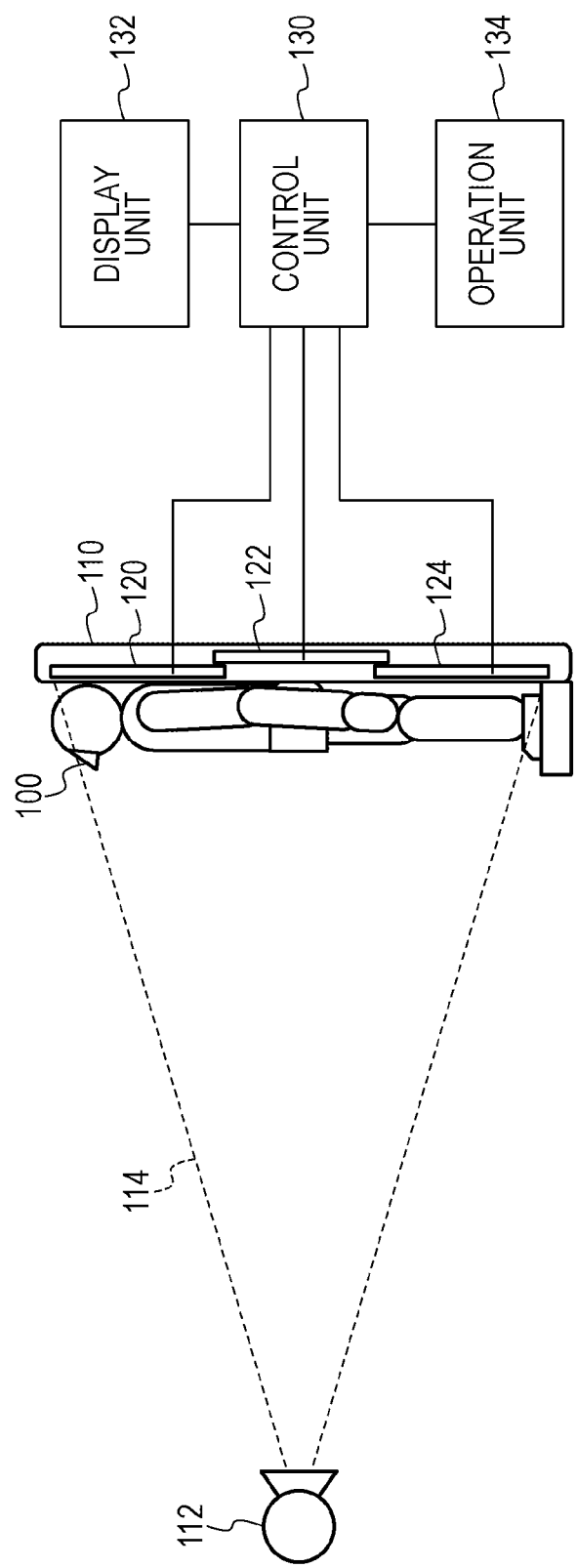
FIG. 1 is a diagram illustrating a schematic configuration of a radiography system of the present invention.

FIG. 1 is a diagram illustrating a schematic configuration of a radiography system of the present invention. This is a diagram illustrating a schematic configuration of a radiography system used in long-sized imaging performed by arranging a plurality of radiation detectors.

The radiography system includes a radiation generator 112, which generates radiation. The radiation generator 112 is capable of irradiating an irradiation range 114 with radiation. The radiation generator 112 is placed with a supporter (not illustrated) interposed therebetween on the floor surface or the ceiling. The irradiation surface of the radiation generator 112 is provided with a diaphragm (not illustrated) that blocks radiation. The operator can set the irradiation range 114 of radiation emitted from the radiation generator 112 by controlling the diaphragm for blocking radiation.

The radiography system includes a plurality of radiation detectors 120, 122, and 124. Although the configuration including the three radiation detectors 120, 122, and 124 is illustrated here, the configuration may include two radiation detectors or four or more radiation detectors. The plurality of radiation detectors 120, 122, and 124 detect radiation that has penetrated a subject 100, and output image data in accordance with the radiation. Note that the image data may also be referred to as radiation images.

Specifically, the plurality of radiation detectors 120, 122, and 124 detect radiation that has penetrated a subject as electric charge corresponding to the penetrating radiation dose. For example, as the plurality of radiation detectors 120, 122, and 124, direct conversion sensors that convert radiation such as a-Se directly into electric charge, or indirect sensors using a scintillator such as CsI and a photoelectric conversion element such as a-Si are used. Furthermore, the plurality of radiation detectors 120, 122, and 124 perform A/D conversion of the detected electric charge to generate image data, and output the image data to a control unit 130.

The plurality of radiation detectors are accommodated in an imaging stand 110. The imaging stand 110 is a rectangular housing, and the inside of the housing is hollow. In addition, the imaging stand 110 has the function of holding the plurality of radiation detectors 120, 122, and 124.

As illustrated in FIG. 1, the imaging stand 110 is erected with respect to the floor surface, and the imaging stand 110 is placed. The subject 100 is placed along the longitudinal direction of the imaging stand 110. The imaging stand 110 has the function of supporting the subject 100.

In FIG. 1, the imaging stand 110 is placed such that the longitudinal direction of the imaging stand 110 is vertical, that is, the imaging stand 110 is upright with respect to the floor surface. Alternatively, the imaging stand 110 may be placed such that the longitudinal direction of the imaging stand 110 is horizontal, that is, the imaging stand 110 is parallel to the floor surface.

In the imaging stand 110, the radiation detector 120, the radiation detector 122, and the radiation detector 124 are arranged along the longitudinal direction of the imaging stand 110. At this time, these radiation detectors are arranged while having some of the radiation detectors overlap each other. For example, as illustrated in FIG. 1, the radiation detector 120 and the radiation detector 122 are arranged such that they partially overlap each other spatially. At this time, the image capturable area of the radiation detector 120 overlaps the image capturable area of the radiation detector 122. Similarly, the radiation detector 122 and the radiation detector 124 are arranged such that they partially overlap each other spatially. At this time, the image capturable area of the radiation detector 122 overlaps the image capturable area of the radiation detector 124. In addition, the radiation detector 122 is arranged on the back side of the radiation detector 120 and the radiation detector 124, that is, at a position farther from the radiation generator 112.

The radiography system also includes the control unit 130, which performs image processing on image data output from a radiation detector, and generates an image; a display unit 132, which displays an image; and an operation unit 134, which is for the operator to give instructions. In addition, the control unit 130 has the function of controlling each element.

The control unit 130 is connected to the plurality of radiation detectors 120, 122, and 124. Specifically, the control unit 130 is connected to the plurality of radiation detectors 120, 122, and 124 via a wired or wireless network or dedicated lines. The plurality of radiation detectors 120, 122, and 124 capture an image of radiation generated by the radiation generator 112, and output image data to the control unit 130. The control unit 130 has the function of applications running on a computer. While controlling the operation of the plurality of radiation detectors 120, 122, and 124, the control unit 130 outputs an image to the display unit 132, or outputs a graphical user interface.

The control unit 130 controls the timing that the radiation generator 112 generates radiation, and conditions for capturing an image of the radiation. In addition, the control unit 130 controls the timing that the plurality of radiation detectors 120, 122, and 124 capture image data, and the timing that the plurality of radiation detectors 120, 122, and 124 output the image data. The control unit 130 is capable of causing the plurality of radiation detectors 120, 122, and 124 to capture images at the same time, and causing the plurality of radiation detectors 120, 122, and 124 to output image data at the same time.

The control unit 130 has the function of performing image processing such as noise removal of image data output from the plurality of radiation detectors 120, 122, and 124. In addition, the control unit 130 can perform image processing such as trimming or rotation of images output from the plurality of radiation detectors 120, 122, and 124. The display unit 132 displays the image output from the control unit 130.

The subject 100 stands on a step placed on the imaging stand 110, and is positioned with respect to the plurality of radiation detectors 120, 122, and 124 and the radiation generator 112. In the present embodiment, radiation is incident at an angle perpendicular to the center of the radiation detector 122. Radiation emitted from the radiation generator 112 to the plurality of radiation detectors 120, 122, and 124 penetrates the subject 100, reaches the plurality of radiation detectors 120, 122, and 124, and is detected. Image data obtained by the plurality of radiation detectors 120, 122, and 124 is combined and processed by the control unit 130 to generate a combined image of the subject 100. The combined image is a long-sized image obtained by long-sized imaging with a wide observation area. The display unit 132 displays a long-sized image output from the control unit 130.

In the radiography system of the present invention, it is possible to perform long-sized imaging of capturing an image of the entire spinal cord or lower legs or the entire body of the subject 100 by one-time radiation irradiation. Radiation (irradiation range 114) emitted from the radiation generator 112 is simultaneously emitted to the plurality of radiation detectors 120, 122, and 124. For example, the operator controls the diaphragm for blocking radiation, or adjusts the distance between the plurality of radiation detectors 120, 122, and 124 and the radiation generator 112.

Note that the plurality of radiation detectors 120, 122, and 124 may have the detection function of automatically detecting the emitting of radiation from the radiation generator 112. The detection function of automatic detection is the function that, in the case where radiation is emitted from the radiation generator 112, the plurality of radiation detectors 120, 122, and 124 detect the radiation and accumulate electric charge caused by the radiation. In the case where any one of the plurality of radiation detectors 120, 122, and 124 detects the emitting of radiation, the plurality of radiation detectors 120, 122, and 124 start the main reading operation and obtain image data.

In the above-described radiography system, the radiation detector 122 is arranged to overlap behind the radiation detectors 120 and 124. For this reason, image data output by the radiation detector 122 has defective areas where structures (structure information) such as a radiation detection panel, a substrate, and a housing, which are the internal elements of the radiation detectors 120 and 124, appear. These defective areas will be described using FIG. 2, which illustrates the relationship between radiation detectors and a radiation image of the radiography system of the present invention.

The radiation detector 120 contains a combination of the following elements stacked in the following order from the radiation incidence face side: a radiation detection panel 150, which detects radiation; an adhesive material 156, which adheres the radiation detection panel 150 and places the radiation detection panel 150 on a panel base 158; the panel base 158, which supports the radiation detection panel 150; and a control substrate 154, which causes an electric signal to be output from the radiation detection panel 150. The radiation detection panel 150 and the control substrate 154 are connected via a flexible substrate 152.

In addition, the external housing of the radiation detector 120 includes a housing 160, which is made of metal or carbon, and a radiation transmissive portion 162, which is made from a radiation transmissive member allowing transmission of radiation. The radiation transmissive portion 162 is placed on the radiation incidence face of the radiation detection panel 150, thereby suppressing attenuation of radiation from the radiation generator 112. The radiation detection panel 150 includes an effective pixel area which can detect radiation, and a marginal area around the outer perimeter of the effective pixel area.

The radiation detector 122 is arranged such that its effective pixel area partially overlap the effective pixel area of the radiation detector 120. In doing so, the configuration allows image information to be reliably obtained at any line of any effective pixel area of the radiation detectors 120 and 122. A long-sized image is generated from image data (radiation image) output from the radiation detector 120 and, out of image data output from the radiation detector 122, image data (radiation image) of an image area whose image data has not been obtained by the radiation detector 120.

Here, one or more structures of the radiation detector 120 appear in image data 302 obtained from the radiation detector 122. An area 410, which is from an end portion of the effective pixel area of the radiation detector 122 to an end portion of the external housing of the radiation detector 122, is an area where one or more structures of the radiation detector 120 appear in image data obtained by the radiation detector 122. A defective area 412 occurs as a result of appearance of one or more structures of the radiation detector 120 in the image data 302 obtained from the radiation detector 122. That is, in a combining processing unit 142, the defective area 412 occurs also in a long-sized image generated from the image data 302 obtained from the radiation detector 122.

The defective area 412 of the image data 302 obtained from the radiation detector 122 includes one or some of the radiation detection panel 150, the flexible substrate 152, the adhesive material 156, the panel base 158, and the housing 160 of the radiation detector 120 as image information. In addition, the defective area 412 includes image information caused by a substrate, screws 414, screws 416, and the like on the flexible substrate 152. Among them, the screws 414 are portions that do not become a defective area in the long-sized image because of the image data 300 obtained from the radiation detector 120. In contrast, the screws 416 are portions that become a defective area.

Note that, although not illustrated, a defective area occurs as a result of appearance of one or more structures of the radiation detector 124 in the image data 302 obtained from the radiation detector 122.

As has been described above, a defective area is a loss of image information caused by a structure whose radiation transmittance is low. Because subject information is lost from the defective area, the defective area may be an obstacle at the time of diagnosis using a long-sized image.

Figure 3:
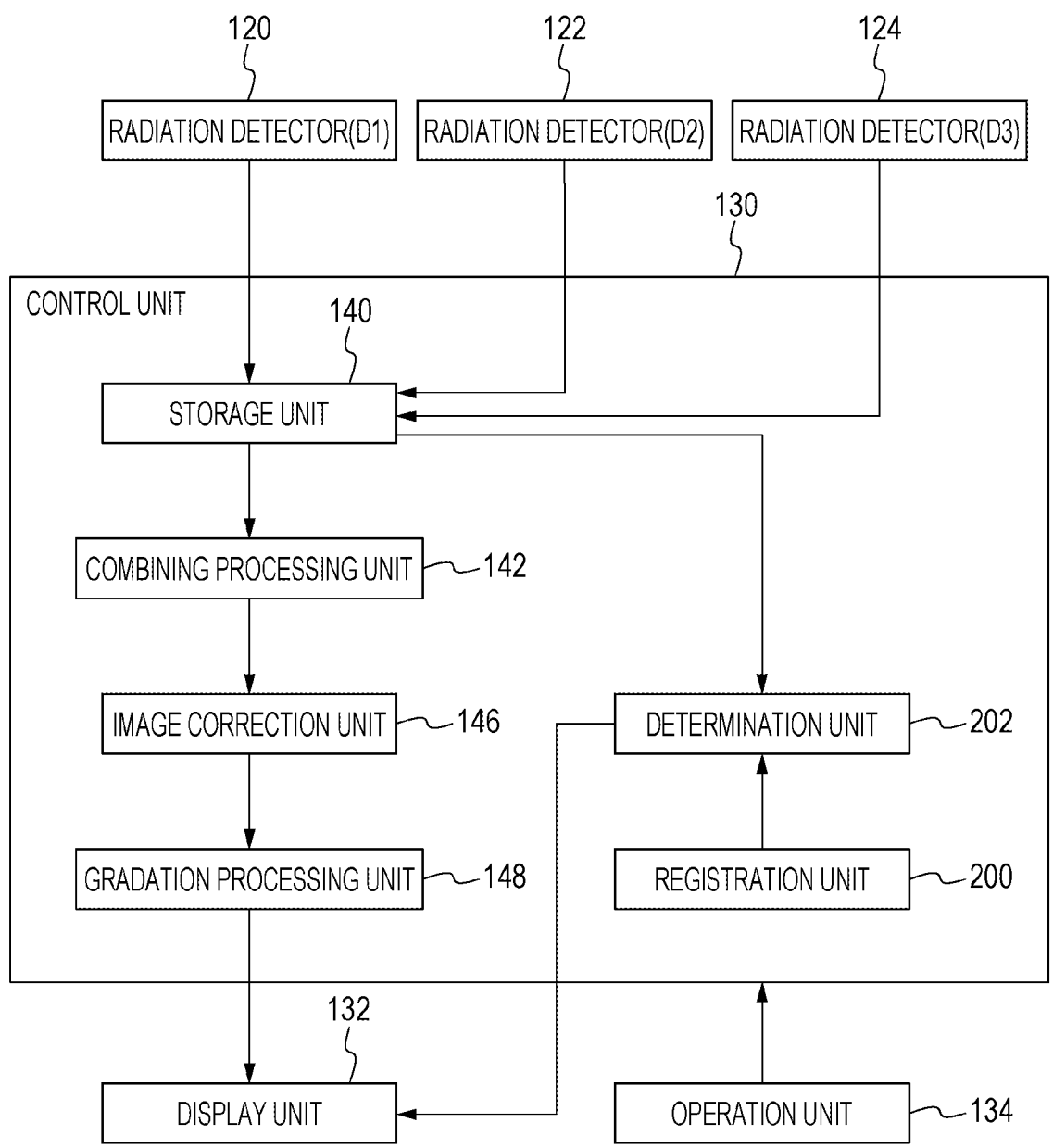
FIG. 3 is a diagram illustrating the configuration of the radiography system (mainly a control unit) of the present invention.

Next, using the diagram of the radiography system of the present invention illustrated in FIG. 3, mainly a configuration for determining whether or not long-sized imaging is possible on the basis of identification information and position information of a plurality of radiation detectors will be described.

The control unit 130 includes a storage unit 140, which stores image data output from the plurality of radiation detectors.

The storage unit 140 stores image data (radiation images) output from the plurality of radiation detectors 120, 122, and 124. As illustrated in FIG. 3, the radiation detectors 120, 122, and 124 are a radiation detector (D1), a radiation detector (D2), and a radiation detector (D3), respectively.

The storage unit 140 can store image data output from the radiation detectors 120, 122, and 124 along with time information. Therefore, with the time information at which the radiation images are obtained, the storage unit 140 can distinguishably store whether or not the radiation images output from the radiation detectors 120, 122, and 124 are obtained at the same time. The storage unit 140 can distinguishably store whether or not the radiation images are radiation images including image information of a subject or radiation images not including image information of a subject.

The operator inputs the position information of the radiation detectors 120, 122, and 124 via the operation unit 134. Note that the imaging stand 110 may include a detector that detects the position information of the plurality of radiation detectors 120, 122, and 124 accommodated in a plurality of accommodation portions. The storage unit 140 can store a plurality of radiation images captured at the same time by the plurality of radiation detectors 120, 122, and 124 in association with the position information (spatial position information) of the radiation detectors. That is, with the position information, a radiation detector arranged at the top, a radiation detector arranged at the center, and a radiation detector arranged at the bottom can be distinguished among the plurality of radiation detectors 120, 122, and 124.

In addition, the storage unit 140 can associatively store that image data output from the radiation detector 120 and image data output from the radiation detector 122 are adjacent to each other. Similarly, the storage unit 140 can associatively store that image data output from the radiation detector 122 and image data output from the radiation detector 124 are adjacent to each other. Furthermore, the storage unit 140 can associatively store that the radiation detector 122 is arranged on the back side of the radiation detectors 120 and 124. The storage unit 140 can output a plurality of items of image data and their position information to the combining processing unit 142.

The control unit 130 includes a registration unit 200, which registers identification information of a plurality of radiation detectors and position information (arrangement information) of a plurality of radiation detectors suitable for long-sized imaging, and a determination unit 202, which determines whether or not long-sized imaging is possible on the basis of the identification information and the position information of the radiation detectors. A plurality of radiation detectors in the present embodiment includes different types of radiation detectors. The identification information includes information on the types of the radiation detectors.

The operator registers, in the registration unit 200 via the operation unit 134, identification information of a plurality of radiation detectors and position information of a plurality of radiation detectors suitable for long-sized imaging. Specifically, the registration unit 200 registers identification information and position information of the radiation detector 120 and the radiation detector 124 suitable for long-sized imaging such that a complicated structure does not appear in image data output from the radiation detector 122 arranged at a position farther from the radiation generator 112. The registration unit 200 registers identification information and position information of the radiation detector 120 and the radiation detector 124 such that radiation detectors for which an image correction unit 146, details of which will be described later, can correct a structure that appears in image data will be arranged at positions closer to the radiation generator 112. In other words, the registration unit 200 registers, as the radiation detector 120 and the radiation detector 124 arranged at positions closer to the radiation generator 112, radiation detectors not including a complicated structure. In this manner, identification information and position information of the radiation detector 120 and the radiation detector 124 arranged at positions closer to the radiation generator 112 are registered in the registration unit 200.

Note that the registration unit 200 may sequentially obtain identification information of radiation detectors using an external network, classify the radiation detectors into those including a complicated structure and those not including a complicated structure, and register each of them. For example, the registration unit 200 may classify the radiation detectors into those for which the image correction unit 146 can correct a structure that appears in image data and those for which the image correction unit 146 is unable to correct a structure that appears in image data, and register each of them.

In the present embodiment, because no other radiation detector is arranged on the back side of the radiation detector 122 arranged at a position farther from the radiation generator 112, there is no need to register identification information and position information of the radiation detector 122 in the registration unit 200. Here, in the case where another radiation detector is arranged on the back side of a radiation detector arranged at a position closer to the radiation generator 112, the registration unit 200 registers identification information and position information of the radiation detector arranged at a position closer to the radiation generator 112.

The registration unit 200 at least outputs the identification information and the position information of the radiation detector 120 and the radiation detector 124 to the determination unit 202.

The determination unit 202 determines whether or not long-sized imaging is possible on the basis of the identification information and the position information of the radiation detector 120 and the radiation detector 124, which are registered in the registration unit 200, and the identification information and the position information of the actually arranged radiation detector 120 and radiation detector 124.

Specifically, the determination unit 202 determines that long-sized imaging is possible in the case where the identification information and the position information of the radiation detector 120 and the radiation detector 124, which are registered in the registration unit 200, match the identification information and the position information of the actually arranged radiation detector 120 and radiation detector 124. The determination unit 202 determines that long-sized imaging is not possible in the case where the identification information and the position information of the radiation detector 120 and the radiation detector 124, which are registered in the registration unit 200, do not match the identification information and the position information of the actually arranged radiation detector 120 and radiation detector 124.

For example, the determination unit 202 determines that long-sized imaging is possible in the case where radiation detectors for which the image correction unit 146 can correct a structure that appears in image data are arranged at positions closer to the radiation generator 112. In short, the determination unit 202 determines that long-sized imaging is possible in the case where radiation detectors not including a complicated structure are arranged at positions closer to the radiation generator 112.

Specific examples of the registration unit 200 and the determination unit 202 will be described using FIGS. 4 and 5. FIG. 4 illustrates the arrangements of a plurality of radiation detectors. Here, it is assumed that type A radiation detector is a radiation detector not including a complicated structure, and type B radiation detector is a radiation detector including a complicated structure. For example, in type A radiation detector, image information caused by the screws 416 or the like does not appear. In type B radiation detector, image information caused by the screws 416 or the like appears.

FIG. 5 illustrates image data based on radiation penetrating each of the radiation detectors in the arrangements illustrated in FIG. 4. In short, the image data illustrated in FIG. 5 is image data detected by a radiation detector arranged on the back side of each of the radiation detectors 120, 122, and 124. From the image data of FIG. 5, it can be concluded that type B radiation detector includes a complicated structure.

Figure 4A:
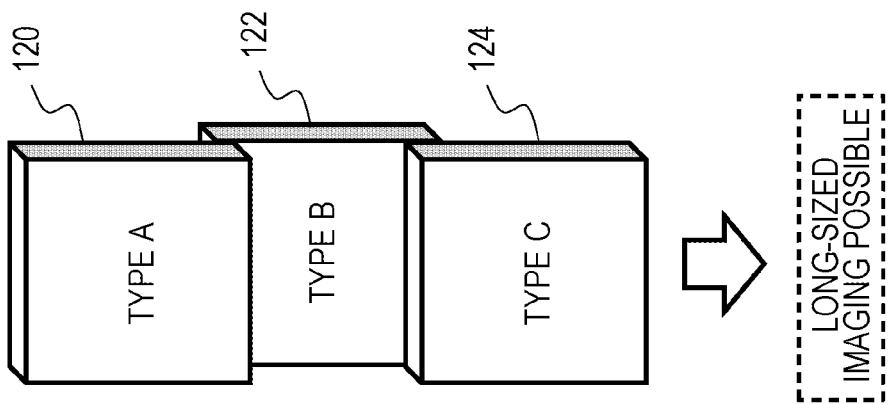
FIG. 4A is a diagram illustrating a specific example of a registration unit and a determination unit of the radiography system of the present invention.
Figure 4B:
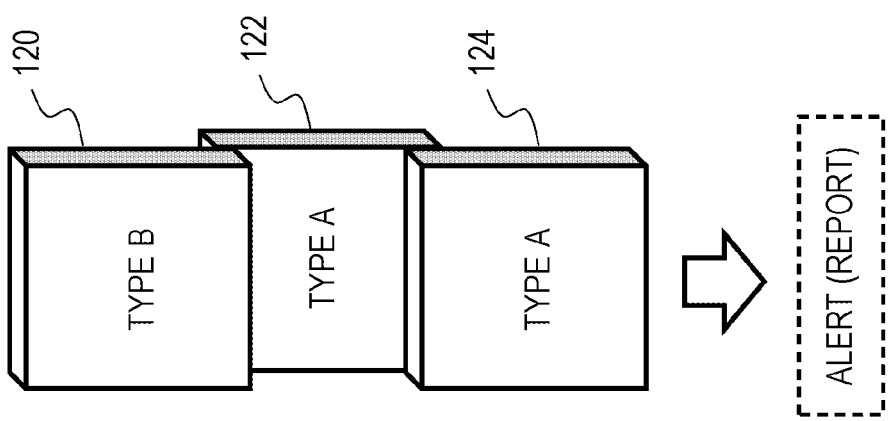
FIG. 4B is a diagram illustrating a specific example of the registration unit and the determination unit of the radiography system of the present invention.
Figure 4C:
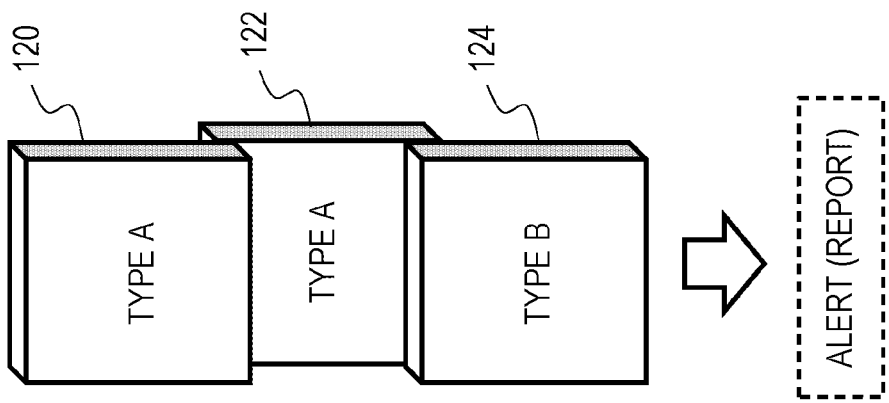
FIG. 4C is a diagram illustrating a specific example of the registration unit and the determination unit of the radiography system of the present invention.
Figure 5A:
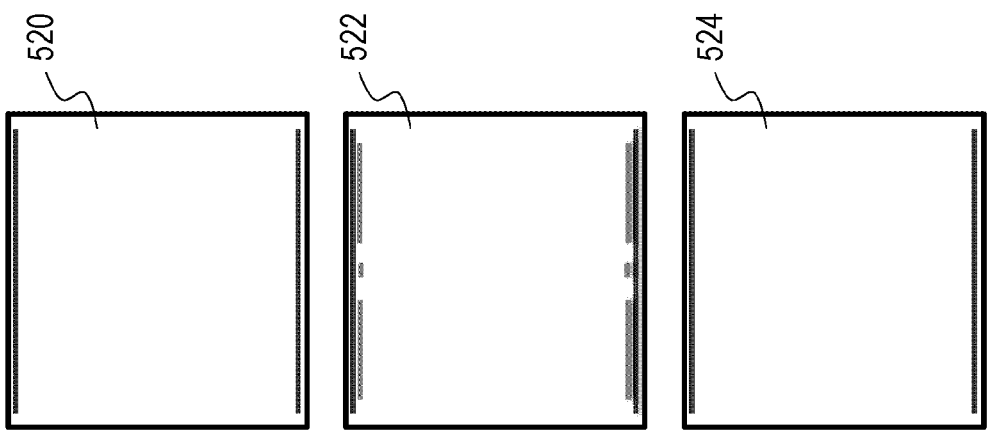
FIG. 5A is a diagram illustrating a specific example of the registration unit and the determination unit of the radiography system of the present invention.
Figure 5B:
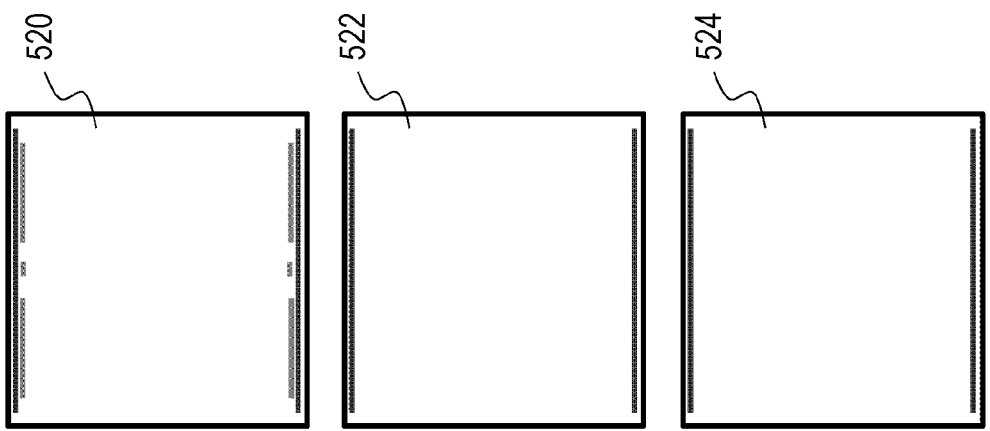
FIG. 5B is a diagram illustrating a specific example of the registration unit and the determination unit of the radiography system of the present invention.
Figure 5C:
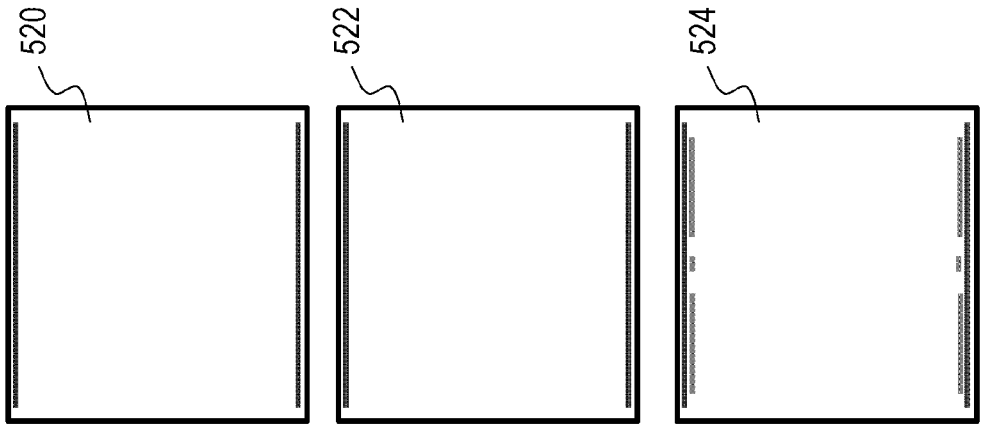
FIG. 5C is a diagram illustrating a specific example of the registration unit and the determination unit of the radiography system of the present invention.

The image data of FIG. 5A corresponds to the arrangement of FIG. 4A. Since type B radiation detector is arranged at the center position in FIG. 4A, it can be concluded that a complicated structure appears in image data 522 at the center in FIG. 5A. Similarly, the image data of FIG. 5B corresponds to the arrangement of FIG. 4B. Since type B radiation detector is arranged at the upper position in FIG. 4B, it can be concluded that a complicated structure appears in image data 520 at the top in FIG. 5B. The image data of FIG. 5C corresponds to the arrangement of FIG. 4C. Since type B radiation detector is arranged at the bottom position in FIG. 4C, it can be concluded that a complicated structure appears in image data 524 at the bottom in FIG. 5C.

The registration unit 200 registers identification information and position information of the radiation detector 120 and the radiation detector 124 such that a complicated structure does not appear in image data output from the radiation detector 122 arranged at a position farther from the radiation generator 112. Here, the registration unit 200 registers the identification information and the position information of the radiation detector 120 and the radiation detector 124 such that type A radiation detectors will be arranged at positions closer to the radiation generator 112. The registration unit 200 may register the identification information and the position information of the radiation detector 122 such that type B radiation detector will be arranged at a position farther from the radiation generator 112.

The storage unit 140 stores the identification information and the position information along with image data obtained from the actually arranged radiation detectors 120, 122, and 124. Note that the identification information and the position information of the radiation detectors 120, 122, and 124 may be input using the operation unit 134.

In the arrangement illustrated in FIG. 4A, type A radiation detectors are arranged at the top and bottom positions in FIG. 4A, and type B radiation detector is arranged at the center position in FIG. 4A.

The storage unit 140 stores the identification information and the position information of the actually arranged radiation detectors 120, 122, and 124, as illustrated in FIG. 4A.

Here, the identification information and the position information of type A radiation detectors are registered in the registration unit 200 such that type A radiation detectors will be arranged at positions closer to the radiation generator 112. Thus, the arrangement illustrated in FIG. 4A allows the actual arrangement of type A radiation detectors at positions closer to the radiation generator 112, the determination unit 202 determines that long-sized imaging is possible.

In the arrangement illustrated in FIG. 4B, type A radiation detectors are arranged at the center and bottom positions in FIG. 4B, and type B radiation detector is arranged at the top position in FIG. 4B.

The storage unit 140 stores the identification information and the position information of the actually arranged radiation detectors 120, 122, and 124, as illustrated in FIG. 4B.

Here, the identification information and the position information of type A radiation detectors are registered in the registration unit 200 such that type A radiation detectors will be arranged at positions closer to the radiation generator 112. Thus, because the arrangement illustrated in FIG. 4B allows the actual arrangement of a type A radiation detector at a position farther from the radiation generator 112 and type B radiation detector at a position closer to the radiation generator 112, the determination unit 202 determines that long-sized imaging is not possible. The display unit 132 alerts (reports to) the operator in the case where long-sized imaging is impossible. The display unit 132 reports that long-sized imaging is unexecutable. Note that the display unit 132 may output sound.

In the arrangement illustrated in FIG. 4C, type A radiation detectors are arranged at the top and center positions in FIG. 4C, and type B radiation detector is arranged at the bottom position in FIG. 4C.

The storage unit 140 stores the identification information and the position information of the actually arranged radiation detectors 120, 122, and 124, as illustrated in FIG. 4C.

Here, the identification information and the position information of type A radiation detectors are registered in the registration unit 200 such that type A radiation detectors will be arranged at positions closer to the radiation generator 112. Thus, because the arrangement illustrated in FIG. 4C allows the actual arrangement of a type A radiation detector at a position farther from the radiation generator 112 and type B radiation detector at a position closer to the radiation generator 112, the determination unit 202 determines that long-sized imaging is not possible. The display unit 132 alerts (reports to) the operator in the case where long-sized imaging is impossible.

It is illustrated in the arrangements illustrated in FIG. 4 that type A radiation detectors are arranged at two positions in FIG. 4, and type B radiation detector is arranged at one position in FIG. 4. The present embodiment may be applied to an arrangement in which type B radiation detectors are arranged at two positions, and type A radiation detector is arranged at one position. The determination unit 202 determines that long-sized imaging is possible in the case where type A radiation detector is arranged at a position closer to the radiation generator 112. The determination unit 202 determines that long-sized imaging is not possible in the case where type A radiation detector is arranged at a position farther from the radiation generator 112.

Note that the determination unit 202 does not perform this determination processing in the case where long-sized imaging is performed using a plurality of radiation detectors that all are of the same type. This is because the plurality of radiation detectors cannot be exchanged and rearranged. In the present embodiment, the determination unit 202 performs this determination processing in the case where long-sized imaging is performed using a plurality of radiation detectors that are of different types. In the case of performing long-sized imaging using a plurality of radiation detectors that are of different types, whether or not long-sized imaging is possible is determined on the basis of identification information and position information of the plurality of radiation detectors.

Figure 6:
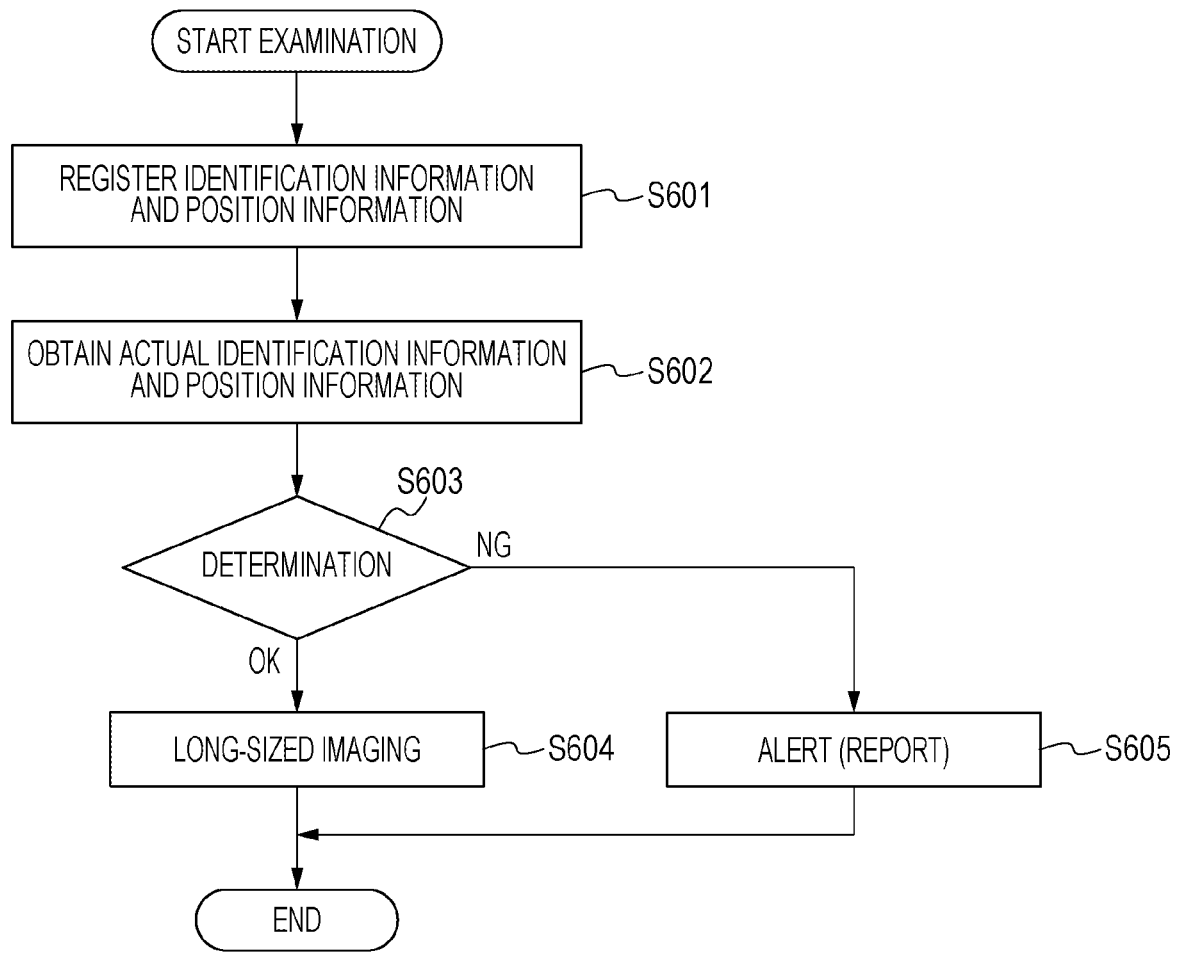
FIG. 6 is a flowchart illustrating the operation of the radiography system of the present invention.

Here, using FIG. 6, a determination procedure of the radiography system will be described using the flowchart of FIG. 6.

Step (S601): the operator registers, in the registration unit 200 using the operation unit 134, identification information and position information of radiation detectors suitable for long-sized imaging. The registration unit 200 registers identification information and position information of radiation detectors suitable for long-sized imaging such that a complicated structure does not appear in image data output from a radiation detector arranged at a position farther from the radiation generator 112.

Step (S602): the operator arranges a plurality of radiation detectors in the imaging stand 110. The operator arranges the plurality of radiation detectors in the imaging stand 110 along the longitudinal direction of the imaging stand 110. Identification information and position information are obtained along with image data obtained from the plurality of radiation detectors that are actually arranged, and the storage unit 140 is caused to store these items of information.

Step (S603): the determination unit 202 determines whether or not long-sized imaging is possible on the basis of the identification information and the position information of the radiation detectors, which are registered in the registration unit 200, and the identification information and the position information of the actually arranged radiation detectors. In the case where long-sized imaging is possible, the procedure proceeds to step (S604). In the case where long-sized imaging is not possible, the procedure proceeds to step (S605).

Step (S604): image capturing preparation is performed using the actually arranged radiation detectors, and long-sized imaging is performed. Image data obtained by the plurality of radiation detectors is combined and processed by the control unit 130 to generate a combined image of the subject 100. The combined image is a long-sized image obtained by long-sized imaging with a wide observation area. The display unit 132 displays the long-sized image output from the control unit 130.

Step (S605): the display unit 132 alerts (reports to) the operator in the case where long-sized imaging is impossible. Note that the actual arrangement of the plurality of the plurality of radiation detectors may be changed, and re-determination may be performed in step (S603).

Figure 2:
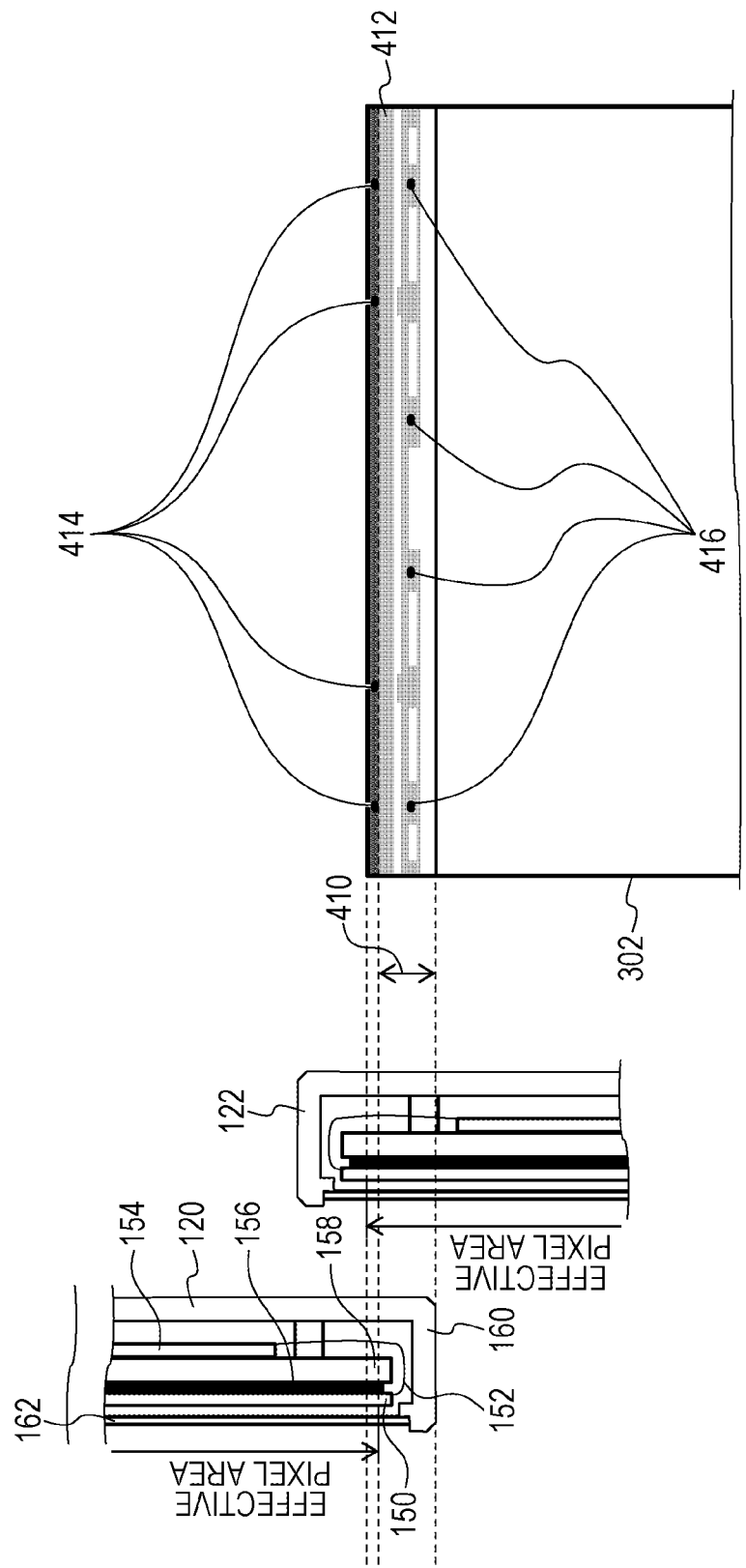
FIG. 2 is a diagram illustrating the relationship between radiation detectors and image data of the radiography system of the present invention.

As illustrated in FIG. 2, the combining processing unit 142 may combine a plurality of items of image data stored in the storage unit 140 to generate a long-sized image. At this time, the combining processing unit 142 combines a plurality of image data including image information of the subject 100 to generate a long-sized image.

The combining processing unit 142 generates a long-sized image by performing the combining on the basis of a plurality of items of image data output from the radiation detectors 120, 122, and 124 and position information. Specifically, the combining processing unit 142 distinguishes a plurality of items of image data (radiation images) output at the same time on the basis of time information from the radiation detectors 120, 122, and 124 as targets to be combined, and combines these items of image data. The combining processing unit 142 determines the positional relationship of the items of image data output from the radiation detectors 120, 122, and 124 on the basis of the position information, and combines the items of image data.

For example, in the example illustrated in FIG. 1, image data output from the radiation detector 120 is positioned above, image data output from the radiation detector 124 is positioned below, and image data output from the radiation detector 122 is positioned therebetween. Furthermore, the items of image data are combined while taking into consideration how these items of image data overlap one another, which is indicated by the position information. For example, defective areas occur at the top and bottom in the radiation detector 122 arranged at a position farther from the radiation generator 112 so as to overlap other radiation detectors. However, no defective area occurs in the radiation detectors 120 and 124. Thus, the combining processing unit 142 can minimize the area of defective areas that occur in a long-sized image by generating the long-sized image using image data generated by the radiation detectors 120 and 124 in a range where radiation detectors overlap. In this manner, the combining processing unit 142 can generate a long-sized image by combining a plurality of items of image data obtained by capturing images of a plurality of image capturing areas that are adjacent to each other.

The image correction unit 146 performs correction processing on a combined image output from the combining processing unit 142 such that defective areas will not be noticeable. Specifically, the image correction unit 146 corrects a defective area using structure information representing a structure in a radiation detector and the pixel value distribution in a normal area adjacent to the defective area. In other words, the image correction unit 146 corrects a defective area in a long-sized image by using information on a normal image area adjacent to the defective area.

Here, structure information is information representing a structure in a radiation detector that may appear in a radiation image. Structure information includes information on the radiation attenuation coefficient, thickness, position, and so forth of a substance present in a radiation detector. In the case of correcting a defective area on a long-sized image, it is expected that the edge of the defective area is correlated with the pixel value distribution of a normal area spatially adjacent to the defective area if there is no appearance. Thus, considering structure information where there is appearance, the image correction unit 146 performs correction such that the pixel value distribution of the defective area approaches the pixel value distribution of the normal area, thereby reducing the defective area.

In order to simplify the description here, a method of obtaining image data captured while arranging a plurality of radiation detectors to overlap each other in the absence of a subject and using the image data as structure information will be described. Structure information is such that appearance of a structure in a radiation detector is represented in the form of a pixel value. This pixel value becomes a small value in a pixel where, for example, a thick structure with a great radiation attenuation coefficient appears, and becomes a large value in a pixel where a thin structure with a small radiation attenuation coefficient does not appear.

Figure 7:
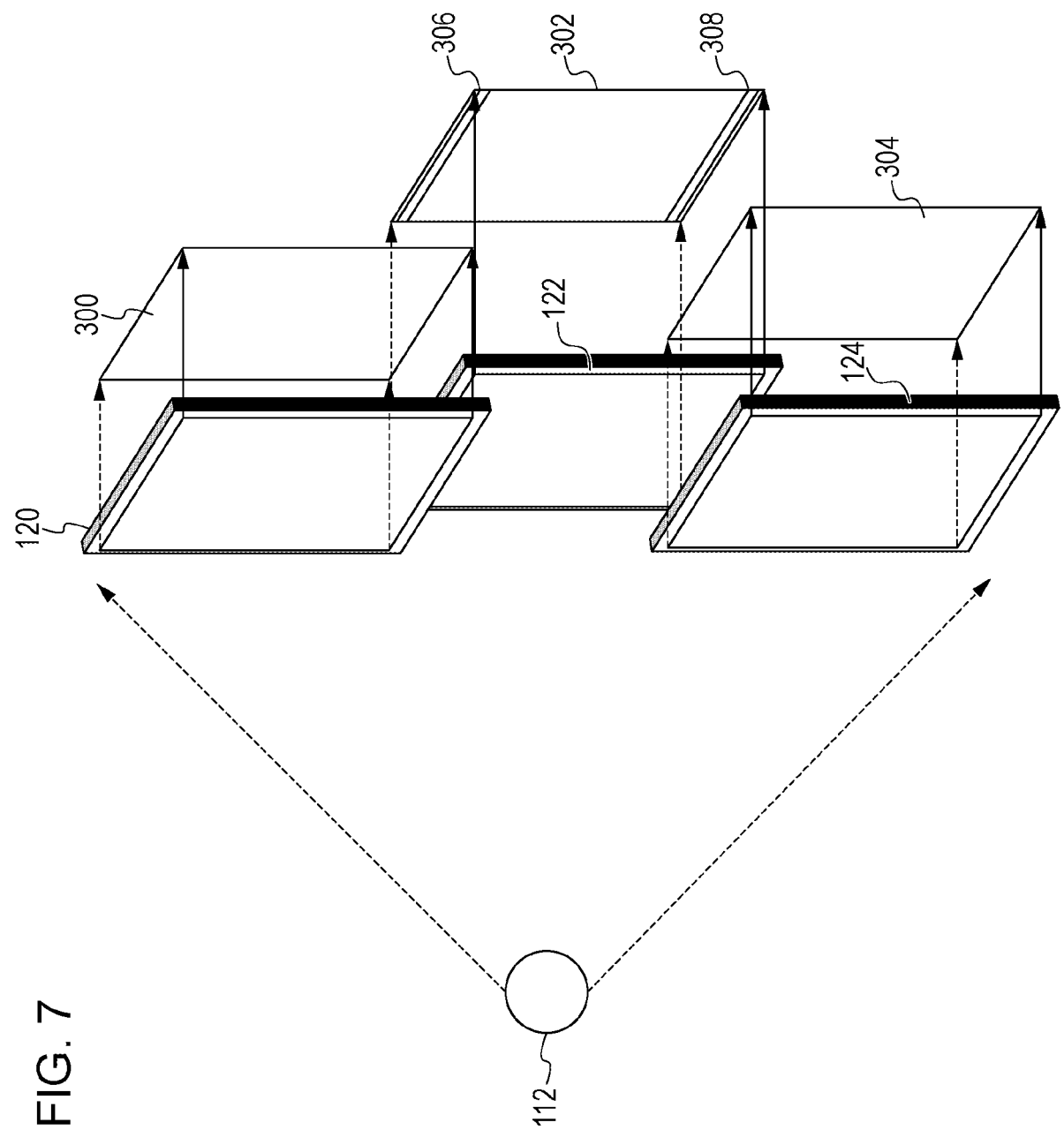
FIG. 7 is a diagram illustrating the relationship between radiation detectors and image data of the radiography system of the present invention.

The case in which image data includes structure information will be described using FIG. 7. FIG. 7 schematically illustrates the structure of the radiography system of the present invention and the form of image data (including a defective area). When the plurality of radiation detectors 120, 122, and 124 are arranged as illustrated in FIG. 7 and images are captured in the absence of a subject, structure information of the radiation detectors 120 and 124 appears in the image data 302 obtained from the radiation detector 122.

Specifically, the image data 302 obtained from the radiation detector 122 includes an appearance area 306 where structure information at the bottom end portion of the overlapping radiation detector 120 appears. In addition, the image data 302 obtained from the radiation detector 122 includes an appearance area 308 where the structure information at the top end portion of the overlapping radiation detector 124 appears.

Note that structure information of another radiation detector does not appear in the image data (radiation image) 300 obtained from the radiation image 120. In addition, structure information of another radiation detector does not appear in the image data (radiation image) 304 obtained from the radiation image 124. Therefore, the image data 302 corresponds to structure data having the manner of appearance on the image as the position/pixel value information. The appearance area 306 and the appearance area 308 may be regarded as structure information.

The position of a defective area on a long-sized image may be obtained from the position information of a radiation detector that the storage unit 140 holds, but may be obtained using structure information. That is, if an information loss occurring on a long-sized image that is indicated by structure information is detected on the long-sized image, that detection area serves as a defective area. For example, in the case of using the above-described appearance areas 306 and 308 as structure information, the image correction unit 146 performs template matching on the long-sized image using the structure information as a template image. The image correction unit 146 obtains a position with the highest correlation as a defective area, and regards this defective area as a target to be corrected.

A gradation processing unit 148 performs gradation processing on a long-sized image obtained by combining a plurality of items of image data (radiation images). Specifically, the gradation processing unit 148 obtains a plurality of items of image data, which are obtained from the radiation detectors 120, 122, and 124, from the storage unit 140. The gradation processing unit 148 analyzes feature amounts of the plurality of items of image data obtained from the radiation detectors 120, 122, and 124, and determines the gradation conversion characteristics of the long-sized image such that the dynamic range of the display unit 132 can be effectively utilized.

The gradation processing unit 148 converts the gradation of the long-sized image using the determined gradation conversion characteristics. Feature amounts each include the histogram, the maximum pixel value, and the minimum pixel value of each item of image data. Feature amounts are calculated by executing analysis processing on the plurality of items of image data obtained from the radiation detectors 120, 122, and 124.

The gradation processing unit 148 can perform gradation processing on a long-sized image corrected by the image correction unit 146. In this manner, because gradation processing is performed on a long-sized image with a reduced defective area, gradation processing on the long-sized image can be appropriately performed. In short, the gradation processing unit 148 can perform gradation processing on a long-sized image while suppressing the influence of appearance of structures of the radiation detector 120 and the radiation detector 124.

The display unit 132 can display a long-sized image with a reduced defective area. In short, the image quality of a long-sized image including appearance of a structure of a radiation detector can be improved.

As described above, according to the present embodiment, the radiography system for generating a long-sized image by combining a plurality of radiation images obtained from the plurality of radiation detectors 120, 122, and 124 includes the determination unit 202, which determines whether or not long-sized imaging is possible on the basis of the identification information and the position information of the plurality of radiation detectors 120, 122, and 124. Thus, long-sized imaging can be performed without degrading the image quality of a long-sized image even in the case where different types of radiation detectors are used.

Second Embodiment

Next, a second embodiment will be described using FIGS. 8 and 9. A point different from the first embodiment is that identification information and position information of the plurality of radiation detectors based on which long-sized imaging is possible are displayed on the display unit 132.

Figure 8A:
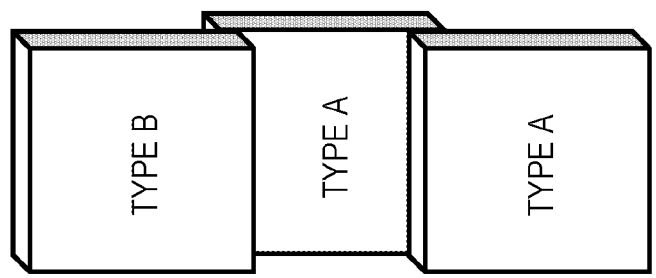
FIG. 8A is a diagram illustrating a second embodiment of the radiography system of the present invention.

In the arrangement illustrated in FIG. 8A, type A radiation detectors are arranged at the center and bottom positions in FIG. 8A, and type B radiation detector is arranged at the top position in FIG. 8A.

Figure 8B:
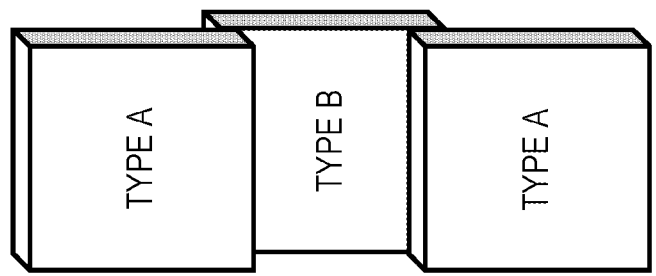
FIG. 8B is a diagram illustrating the second embodiment of the radiography system of the present invention.

Because type A radiation detector is actually arranged at a position farther from the radiation generator 112 and type B radiation detector is actually arranged at a position closer to the radiation generator 112 in the arrangement illustrated in FIG. 8A, the determination unit 202 determines that long-sized imaging is not possible. The control unit 130 causes the display unit 132 to display identification information and position information of the plurality of radiation detectors based on which long-sized imaging is possible. Here, as illustrated in FIG. 8B, the display unit 132 is caused to display that type A radiation detectors are arranged at the top and bottom positions, and type B radiation detector is arranged at the center position.

Figure 9:
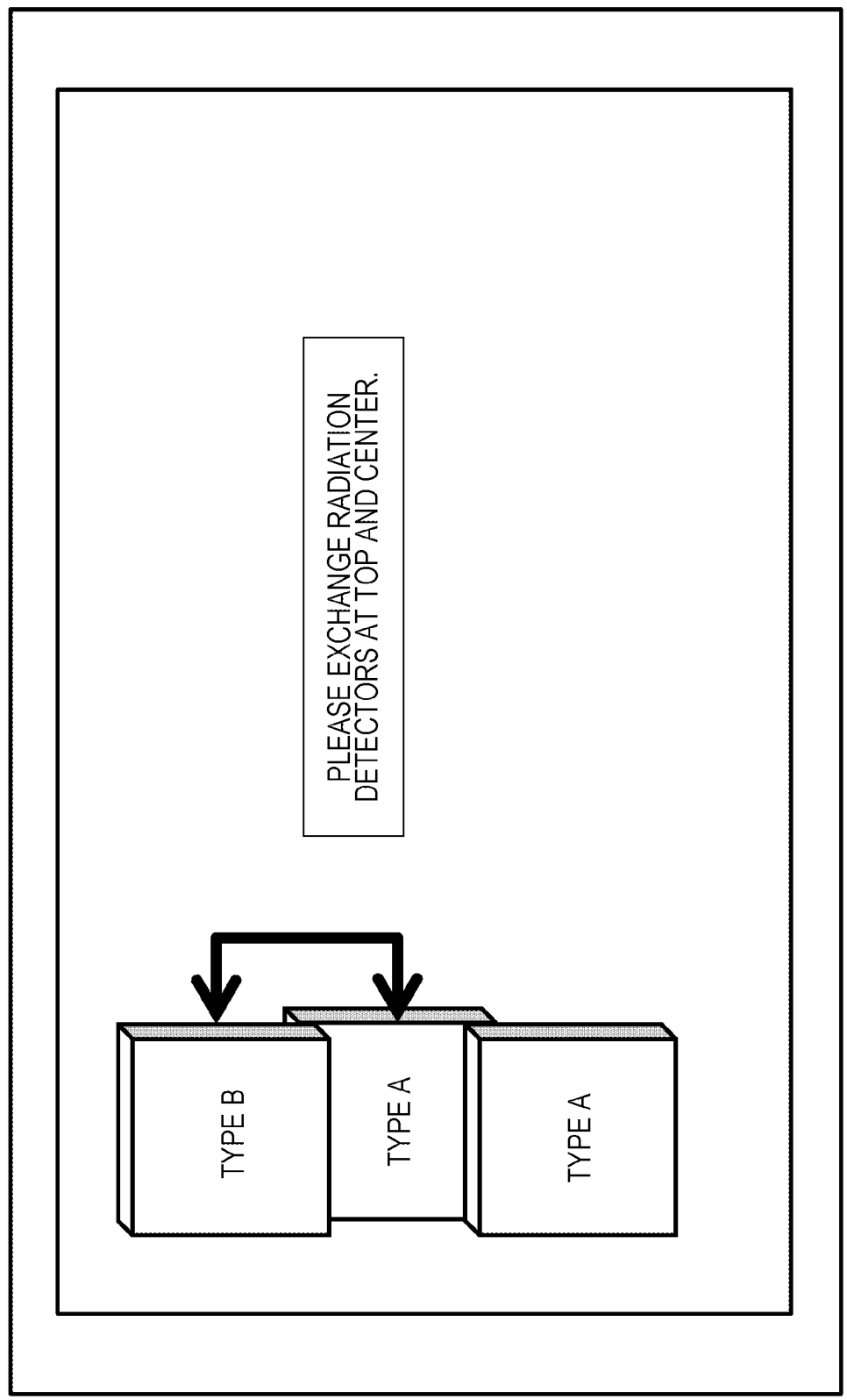
FIG. 9 is a diagram illustrating the second embodiment of the radiography system of the present invention.

Specifically, as illustrated in FIG. 9, a message such as "Please exchange radiation detectors at the top and the center" or symbols such as arrows are displayed on the display unit 132. Thus, the operator can arrange type A radiation detectors at the top and bottom positions and arrange type B radiation detector at the center position.

Note that, in preparation for long-sized imaging, identification information of a plurality of radiation detectors and position information (arrangement information) of a plurality of radiation detectors suitable for long-sized imaging, which are registered in the registration unit 200, may be displayed on the display unit 132.

Thus, long-sized imaging can be performed without degrading the image quality of a long-sized image even in the case where different types of radiation detectors are used.

The present invention is not construed to be limited to the above-described embodiments, and various changes and alterations can be made without departing from the spirit and scope of the present invention. Therefore, the following claims are appended in order to make the scope of the present invention public.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiography system for generating a long-sized image by combining a plurality of items of image data obtained from radiation detectors, comprising:
a determination unit that determines whether or not long-sized imaging is possible based on identification information and position information of the radiation detectors of different types, wherein each of the radiation detectors of different types includes an effective pixel area which can detect radiation and includes, as each of the different types, each of different structures which is provided at at least a part of an outer perimeter of the effective pixel area,
wherein the determination unit determines that the imaging is possible in a case where a first radiation detector of the radiation detectors is disposed at a position farther from a radiation generator than a second radiation detector of the radiation detectors, wherein the first radiation detector includes a complicated structure and the second radiation detector does not include the complicated structure.

2. The radiography system according to claim 1, wherein, in a case of performing long-sized imaging using the detectors of different types, the determination unit determines whether or not long-sized imaging is possible based on identification information and position information of the radiation detectors of different types.

3. The radiography system according to claim 1, wherein the identification information includes types of the radiation detectors of different types.

4. The radiography system according to claim 1, comprising:
a registration unit that registers identification information and position information of the radiation detectors of different types,
wherein the determination unit determines that long-sized imaging is not possible in a case where the identification information and the position information of the radiation detectors of different types, which are registered in the registration unit, do not match identification information and position information of the radiation detectors of different types that are actually arranged.

5. The radiography system according to claim 4, wherein the determination unit determines that long-sized imaging is possible in a case where the identification information and the position information of the radiation detectors of different types, which are registered in the registration unit, match identification information and position information of the radiation detectors of different types that are actually arranged.

6. The radiography system according to claim 4, comprising: a display unit that reports to an operator in a case where the determination unit determines that long-sized imaging is not possible.

7. The radiography system according to claim 6, wherein the display unit displays identification information and position information of the radiation detectors of different types based on which long-sized imaging is possible.

8. The radiography system according to claim 4, wherein the registration unit registers identification information and position information of the radiation detectors of different types such that a complicated structure does not appear in image data output from a radiation detector arranged at a position farther from a radiation generator that generates radiation.

9. The radiography system according to claim 1, comprising: an image correction unit that corrects a structure that appears in image data output from the radiation detector.

10. The image processing apparatus according to claim 1, wherein the complicated structure includes a screw.

11. The radiography system according to claim 1, wherein, other than the first radiation detector, none of the radiation detectors include the complicated structure.

12. The radiography system according to claim 1,
wherein the complicated structure has a large radiation attenuation coefficient,
wherein the complicated structure occupies a region located in the outer perimeter of the effective pixel area, between an edge of the effective pixel area and an edge of the first radiation detector, such that the region has a large radiation attenuation coefficient, and
wherein the region that has the large radiation attenuation coefficient is larger than a respective region between the outer perimeter of the effective pixel area and an edge of the second radiation detector.

13. The radiography system according to claim 1, wherein, from a perspective of the radiation generator, a relative portion of a total area of the first radiation detector that is occupied by the effective pixel area is smaller than a relative portion of a total area of the second radiation detector that is occupied by the respective effective pixel area.

14. An image processing method for generating an image by combining a plurality of items of image data obtained from radiation detectors, comprising:
determining whether or not an imaging is possible based on identification information and position information of the radiation detectors of different types, wherein each of the radiation detectors of different types includes an effective pixel area which can detect radiation and includes, as each of the different types, each of different structures which is provided at at least a part of an outer perimeter of the effective pixel area,
wherein it is determined that the imaging is possible in a case where a first radiation detector of the radiation detectors is disposed at a position farther from a radiation generator than a second radiation detector of the radiation detectors, wherein the first radiation detector includes a complicated structure and the second radiation detector does not include the complicated structure.

15. A non-transitory computer-readable storage medium storing a program for causing a computer to execute the method according to claim 14.

16. An image processing apparatus for generating an image by combining a plurality of items of image data obtained from radiation detectors, comprising:
a determination unit that determines whether or not an imaging is possible based on identification information and position information of the radiation detectors of different types, wherein each of the radiation detectors of different types includes an effective pixel area which can detect radiation and includes, as each of the different types, each of different structures which is provided at at least a part of an outer perimeter of the effective pixel area,
wherein the determination unit determines that the imaging is possible in a case where a first radiation detector of the radiation detectors is disposed at a position farther from a radiation generator than a second radiation detector of the radiation detectors, wherein the first radiation detector includes a complicated structure and the second radiation detector does not include the complicated structure.

17. The image processing apparatus according to claim 16, wherein the imaging is performed in a state in which the radiation detectors of different types are arranged along a longitudinal direction of an imaging stand and in which the radiation detectors of different types partially overlap each other.

18. The image processing apparatus according to claim 16, wherein the complicated structure being a structure included in an area between an end portion of an effective pixel area of the radiation detector and an end portion of an external housing of the radiation detector.

19. The image processing apparatus according to claim 16, wherein the complicated structure includes a screw.

* * * * *